United States Patent
Mansfield et al.

(10) Patent No.: US 11,172,947 B2
(45) Date of Patent: Nov. 16, 2021

(54) ENDOSCOPE TOOL

(71) Applicant: GYRUS ACMI, INC., Southborough, MA (US)

(72) Inventors: Richard P. Mansfield, Sterling, MA (US); Judy L. Walish, West Roxbury, MA (US); Stephen P. Femia, Holden, MA (US)

(73) Assignee: Gyrus Acmi, Inc., Westborough, MA (US)

( * ) Notice: Subject to any disclaimer, the term of this patent is extended or adjusted under 35 U.S.C. 154(b) by 33 days.

(21) Appl. No.: 16/081,095

(22) PCT Filed: Mar. 9, 2016

(86) PCT No.: PCT/IB2016/051346
§ 371 (c)(1),
(2) Date: Aug. 30, 2018

(87) PCT Pub. No.: WO2017/153806
PCT Pub. Date: Sep. 14, 2017

(65) Prior Publication Data
US 2019/0069915 A1    Mar. 7, 2019

(51) Int. Cl.
*A61B 17/22*    (2006.01)
*A61B 17/221*    (2006.01)
(Continued)

(52) U.S. Cl.
CPC ........ *A61B 17/221* (2013.01); *A61B 1/00085* (2013.01); *A61B 1/00133* (2013.01);
(Continued)

(58) Field of Classification Search
CPC .......... A61B 17/221; A61B 2017/0367; A61B 1/0085; A61B 1/00133; A61B 2017/00477
See application file for complete search history.

(56) References Cited

U.S. PATENT DOCUMENTS 3,955,578 A    5/1976    Chamness et al.
4,691,705 A    9/1987    Okada ........................ 128/328
(Continued)

FOREIGN PATENT DOCUMENTS

CN    108601600 A    9/2018
EP    3416570 B1    3/2020
(Continued)

OTHER PUBLICATIONS

"Chinese Application Serial No. 201680081223.2, Office Action dated Oct. 10, 2020", with English translation, 14 pgs.
(Continued)

*Primary Examiner* — Alexander J Orkin
(74) *Attorney, Agent, or Firm* — Schwegman Lundberg & Woessner, P.A.

(57) ABSTRACT

A tool for use by a surgeon for operating a basket device for capturing an object to be removed from a body of an animal. The tool includes a first controller and a second controller. The first controller is adapted to be coupled to the basket device for selectively controlling the basket device and moving the basket device between a first, closed position and a second, open position. The first controller includes a plunger and cylinder mechanism; and a handle coupled to the plunger for operating the relative position of the plunger with respect to the cylinder. The second controller is positioned adjacent to the first controller and adapted to be coupled to the basket device for selectively independently controlling the rotation of the relative to the first controller.

12 Claims, 8 Drawing Sheets

(51) Int. Cl.
*A61B 1/00* (2006.01)
*A61B 17/00* (2006.01)
(52) U.S. Cl.
CPC .............. *A61B 2017/0042* (2013.01); *A61B 2017/0046* (2013.01); *A61B 2017/00367* (2013.01); *A61B 2017/00477* (2013.01)

(56) References Cited

U.S. PATENT DOCUMENTS

| | | | |
|---|---|---|---|
| 5,147,303 | A | 9/1992 | Martin .................... 604/110 |
| 5,403,324 | A | 4/1995 | Ciervo et al. ............ 606/128 |
| 5,720,754 | A | 2/1998 | Middleman et al. ..... 606/127 |
| 6,053,934 | A | 4/2000 | Andrews et al. ......... 606/207 |
| 6,228,023 | B1* | 5/2001 | Zaslavsky ........... A61B 17/221 600/204 |
| 6,419,679 | B1 | 7/2002 | Dhindsa .................. 606/127 |
| 6,764,499 | B2 | 7/2004 | Honey et al. ............ 606/207 |
| 7,744,583 | B2 | 6/2010 | Seifert et al. ............ 604/507 |
| 8,211,115 | B2 | 7/2012 | Cheng et al. ............ 606/114 |
| 8,608,690 | B2 | 12/2013 | Pal ....................... 604/103.04 |
| 2003/0009176 | A1* | 1/2003 | Bilitz .................. A61B 17/221 606/127 |
| 2003/0109889 | A1* | 6/2003 | Mercereau ........... A61B 17/221 606/127 |
| 2008/0188890 | A1 | 8/2008 | Weitzner et al. ........ 606/205 |
| 2009/0157060 | A1 | 6/2009 | Teague et al. ............... 606/1 |
| 2012/0095477 | A1 | 4/2012 | Bilitz ...................... 606/127 |
| 2013/0035695 | A1 | 2/2013 | Uihlein .................... 606/127 |
| 2013/2111415 | | 8/2013 | Zerfas et al. ............ 606/114 |
| 2014/0257253 | A1 | 9/2014 | Jemison |
| 2016/0008015 | A1* | 1/2016 | Nguyen ............. A61B 17/221 606/127 |

FOREIGN PATENT DOCUMENTS

| | | | |
|---|---|---|---|
| EP | 3656318 | A1 | 5/2020 |
| GB | 809773 | | 10/1956 |
| JP | H10192286 | A | 7/1998 |
| JP | 11113917 | A | 4/1999 |
| JP | 2005230132 | A | 9/2005 |
| JP | 2006204745 | A | 8/2006 |
| JP | 2012161638 | A | 8/2012 |
| JP | 2019509090 | A | 4/2019 |
| JP | 2020073196 | A | 5/2020 |
| WO | WO 2004/069059 | A2 | 8/2004 |
| WO | WO 2016/061297 | A1 | 4/2016 |
| WO | WO-2017153806 | A1 | 9/2017 |

OTHER PUBLICATIONS

"European Application Serial No. 19218914.0, Response filed Nov. 14, 2020 to Extended European Search Report dated Apr. 6, 2020", 4 pgs.

"International Application Serial No. PCT/IB2016/051346, Invitation to Pay Additional Fees dated Nov. 7, 2016", 7 pgs.

"Japanese Application Serial No. 2018-542138, Response filed Jan. 13, 2021 to Decision of Final Refusal dated Sep. 14, 2020", with translation of claims and machine translation, 25 pgs.

"European Application Serial No. 16713092.1, Intention to Grant dated Nov. 13, 2019", 30 pgs.

"European Application Serial No. 16713092.1, Response to Communication pursuant to Rules 161(1) and 162 EPC filed Mar. 8, 2019", 37 pgs.

"European Application Serial No. 19218914.0, Extended European Search Report dated Apr. 6, 2020", 4 pgs.

"International Application Serial No. PCT/IB2016/051346, International Preliminary Report on Patentability dated Sep. 20, 2018", 12 pgs.

"International Application Serial No. PCT/IB2016/051346, International Search Report dated Jan. 16, 2017", 6 pgs.

"International Application Serial No. PCT/IB2016/051346, Written Opinion dated Jan. 16, 2017", 10 pgs.

"Japanese Application Serial No. 2018-542138, Examiners Decision of Final Refusal dated Sep. 14, 2020", 5 pgs.

"Japanese Application Serial No. 2018-542138, Notification of Reasons for Refusal dated May 11, 2020".

"Japanese Application Serial No. 2018-542138, Notification of Reasons for Refusal dated Nov. 18, 2019", 8 pgs.

"Japanese Application Serial No. 2018-542138, Response filed Feb. 18, 2020 to Notification of Reasons for Refusal dated Nov. 18, 2019", 12 pgs.

"Japanese Application Serial No. 2018-542138, Response filed Jul. 28, 2020 to Notification of Reasons for Refusal dated May 11, 2020", 8 pgs.

"Chinese Application Serial No. 201680081223.2, Response filed Feb. 25, 2021 to Office Action dated Oct. 10, 2020", w/English Claims, 11 pgs.

"Japanese Application Serial No. 2020-025258, Notification of Reasons for Refusal dated Feb. 22, 2021", 6 pgs.

"Chinese Application No. 201680081223.2, Office Action Jul. 22, 2021", W/English Translation, 8 pgs.

"Japanese Application Serial No. 2020-025258, Response filed May 18, 2021 to Notification of Reasons for Refusal dated Feb. 22, 2021", w/ English Claims and machine translation, 12 pgs.

"Chinese Application Serial No. 201680081223.2, Response filed Oct. 8, 2021 to Office Acton dated Jul. 22, 2021", with English translation of claims, 9 pgs.

"Japanese Application Serial No. 2018-542138, Notification of Reasons for Refusal dated Sep. 13, 2021", w/ English Transnlation, 7 pgs.

* cited by examiner

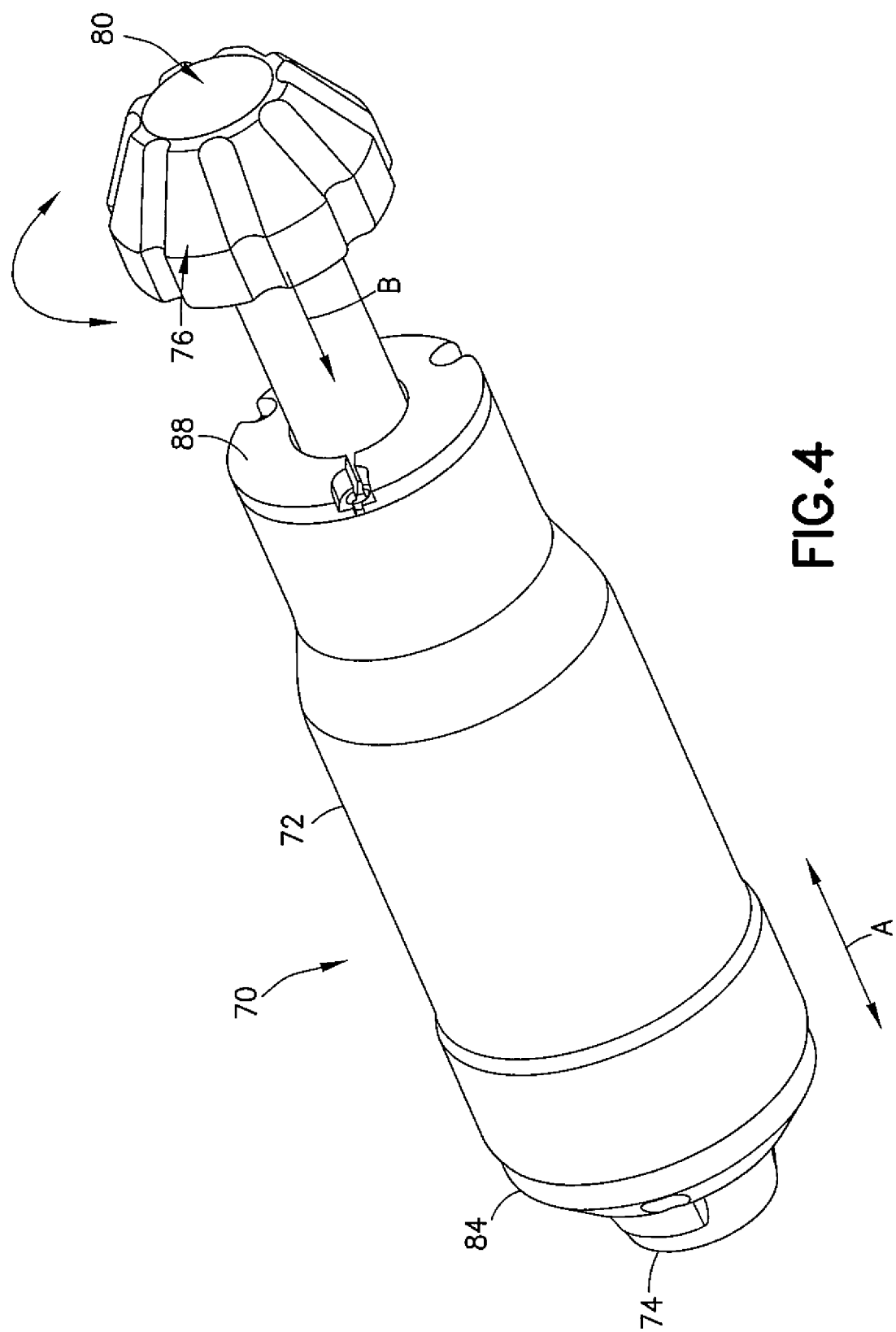

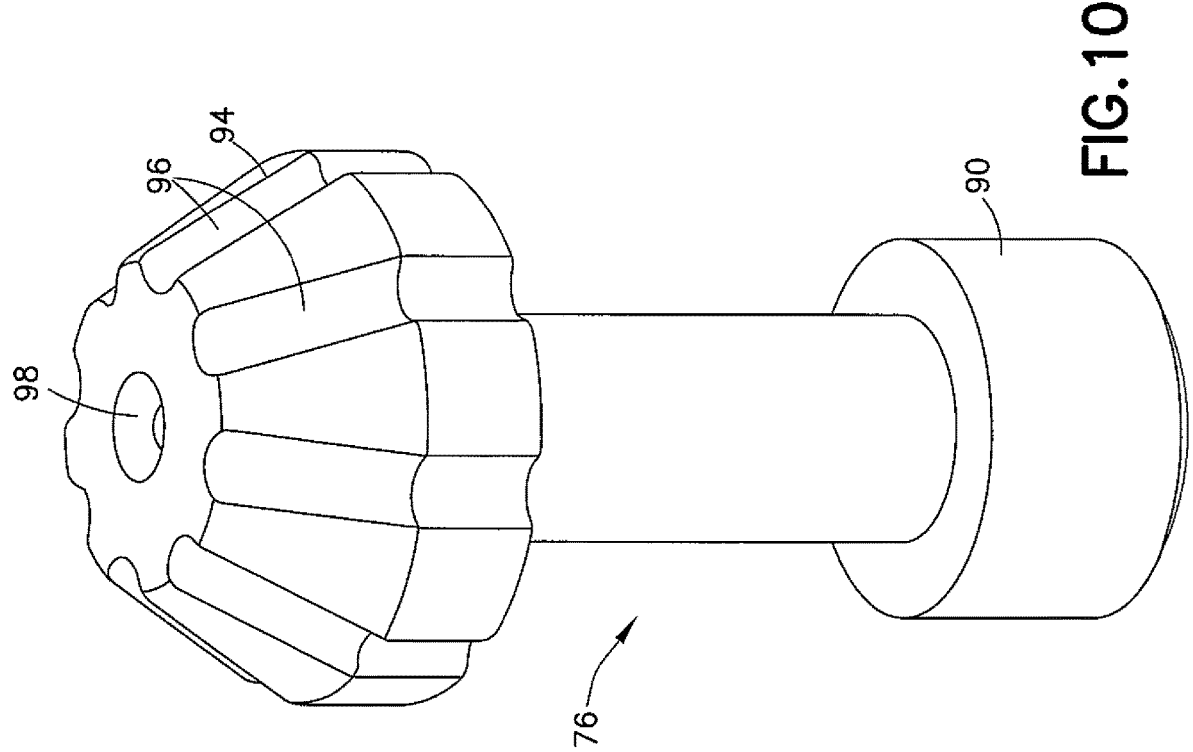
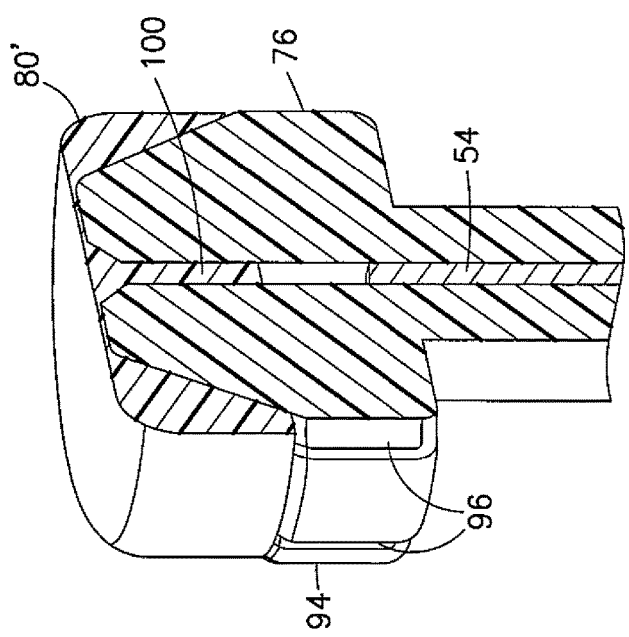

ENDOSCOPE TOOL

This patent application is a U.S. National Stage application of International Patent Application Number PCT/IB2016/051346 filed Mar. 9, 2016, which is hereby incorporated by reference in its entirety.

BACKGROUND

Technical Field

The exemplary and non-limiting embodiments relate generally to an endoscope and, more particularly, to an apparatus used with an endoscope.

Brief Description of Prior Developments

U.S. Pat. No. 6,764,499 discloses a medical device with a basket. U.S. Pat. No. 8,211,115 discloses a variable size retrieval basket.

SUMMARY

The following summary is merely intended to be exemplary. The summary is not intended to limit the scope of the claims.

In accordance with one aspect, an example embodiment may be provided in a tool for use by a surgeon for operating a basket device for capturing an object to be removed from a body of an animal, the tool comprising: a first controller adapted to be coupled to the basket device for selectively controlling the basket device and moving the basket device between a first, closed position and a second, open position, the first controller comprising: a plunger and cylinder mechanism; and a handle coupled to the plunger for operating the relative position of the plunger with respect to the cylinder; and a second controller positioned adjacent to the first controller and adapted to be coupled to the basket device for selectively controlling the rotation of the basket device independent of the first controller.

In accordance with another aspect, an example embodiment may be provided in a tool for use by a surgeon for operating a basket device for capturing an object to be removed from a body of an animal, the tool comprising a housing having a longitudinal axis and including a passage; a first controller including a first portion located in the passage in the housing and a second portion extending from the housing; wherein the first controller is adapted to be coupled to the basket device for selectively controlling the basket device and wherein the first controller is axially movable in the passage of the housing for moving the basket device between a first, closed position and a second, open position, and wherein the first controller is rotationally movable in the passage of the housing for rotating the basket device when in the second, open position; and an end surface coupled to the second portion of the first controller wherein the end surface moves axially with the first controller and wherein the end surface moves independently rotationally of the first controller such that the end surface may remain rotationally stationary while the first controller is rotated.

BRIEF DESCRIPTION OF THE DRAWINGS

The foregoing aspects and other features are explained in the following description, taken in connection with the accompanying drawings, wherein:

FIG. 4 is a perspective view of a proximal end of the endoscopic tool shown in FIGS. 2-3;
FIG. 9 is a partial cross sectional view of the top button and plunger shown in FIG. 8;
FIG. 10 is a perspective view of the plunger shown in FIGS. 4, 6 and 8.

DETAILED DESCRIPTION OF EMBODIMENTS

Figure 1:
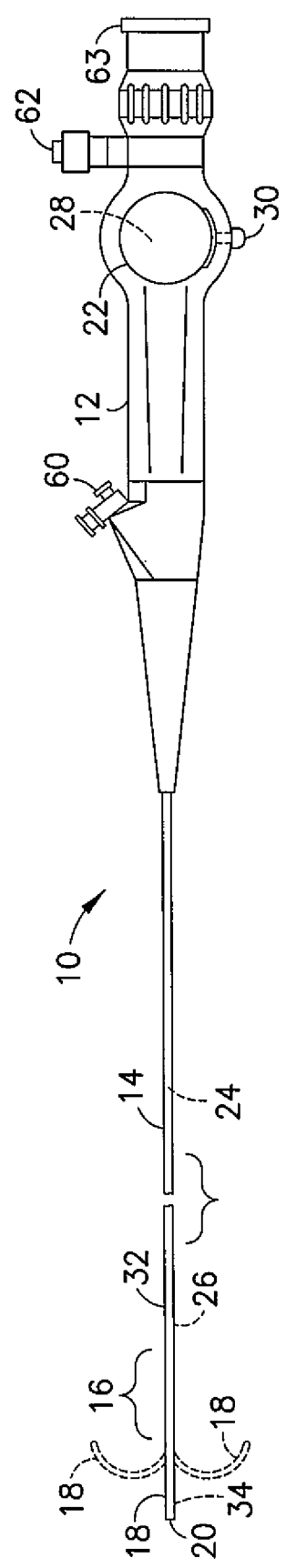
FIG. 1 is a side view of an endoscope.

Referring to FIG. 1, there is shown a side view of an example apparatus 10. The apparatus 10 in this example is an endoscope medical device configured to be partially inserted into a patient's body, such as in through the patient's urethra for example. The endoscope generally comprises a control section 12 and a flexible or semi-flexible shaft 14 connected to the control section 12. In this example the control section forms a handle for the apparatus. The shaft 14 includes a passive deflection section 16 and an active deflection section (bending section) 18 at the distal end of the shaft 14. A control system 22 to control the active deflection section 18 extends from the control section 12 to the active deflection section 18. The control system 22 generally comprises bending control wires, wire sheaths, and an actuator 28. The wires are connected to the actuator 28 at one end and are connected to the active deflection section 18 at a second end.

In the example embodiment shown, the control section 12 has a user operated slide or lever (control lever) 30. The lever 30 is connected to the actuator 28. The actuator 28 is adapted to pull and release the wires of the control system 22. When the lever 30 is moved by the user, the actuator 28 is moved. The actuator 28 may be, for example, a drum or pulley rotatably connected to the control section 12 to pull one wire while releasing the other. In an alternate embodiment, the actuator may be any suitable type of device, such as a rocker arm adapted to pull and release the wires of the control system 22. In another alternate embodiment, where the control system may have two or more pairs of control wires, the control section will have additional actuators and corresponding controls to drive the additional pairs of bending control wires. In still other alternate embodiments, the control section may have knobs with rack and pinion mechanisms or other suitable user operated controls for the control system.

The shaft 14 is cantilevered from the control section 12. The flexible shaft 14 includes the bending control wires of the control system 22, a fiber optical image bundle, a fiber optical illumination bundle, and a working channel. A port 60 for inserting instruments into the working channel 24 of the shaft is located on the control section 12. The control section 12 also has a light source post 62 for connecting a light source (not shown) to the illumination bundle. In addition, the control section 12 has an eyepiece 63 for a user to view an image transmitted by the image bundle from the front end 20. In alternate embodiments, the flexible shaft may house different systems within. The shaft 14 generally comprises a frame 26, a cover 32 and an objective head 34.

Figure 2:
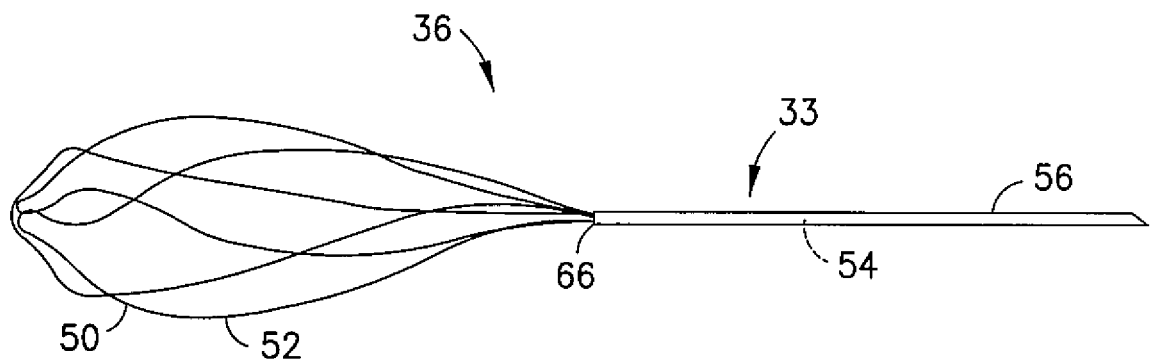
FIG. 2 is a side view of a distal end of an endoscopic tool.
Figure 3:
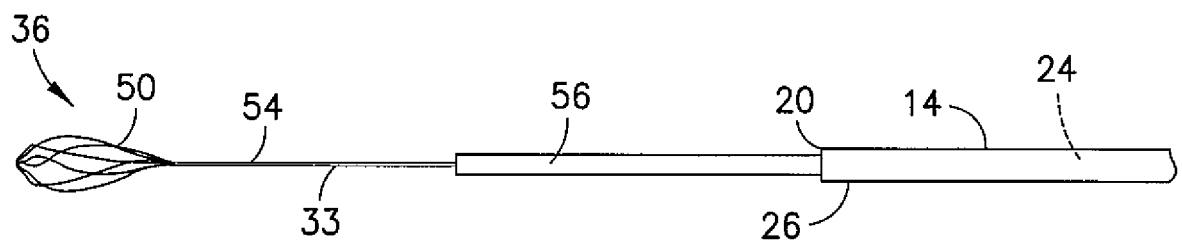
FIG. 3 is a side view illustrating extension of the tool shown in FIG. 2 from the distal end of the endoscope shown in FIG. 1.

Referring also to FIGS. 2-3, a distal end of an endoscopic tool 36 is shown. The tool 36 is attached to the apparatus 10 and is configured to extend out of the distal end 20 of the shaft 14 from the working channel 24. The tool 36, in this example, is a Surgeon Controlled Basket Device (SCBD). The tool 36 includes an assembly 33 which comprises a basket device 50 and a sheath 56. The basket device 50 comprises a basket section 52 at a distal end, and a shaft section 54 extending through the sheath 56 to a proximal end of the tool 36. The shaft section 54 functions as a control wire for moving the basket section 52. The sheath 56 and basket device 50 are longitudinally movable relative to each other to move the basket device 50 between a forward position and a rearward position relative to the sheath 56. FIGS. 2 and 3 show the shaft section (control wire) 54 moved forward relative to the sheath 56 such that the basket section 52 is located out from a front end aperture 66 of the sheath 56. In the forward position of the sheath 56 on the basket device 50, the basket section 52 is located inside the sheath 56; the basket section 52 being collapsed by the sheath 56 into a smaller shape to fit inside the sheath 56.

Figure 5:
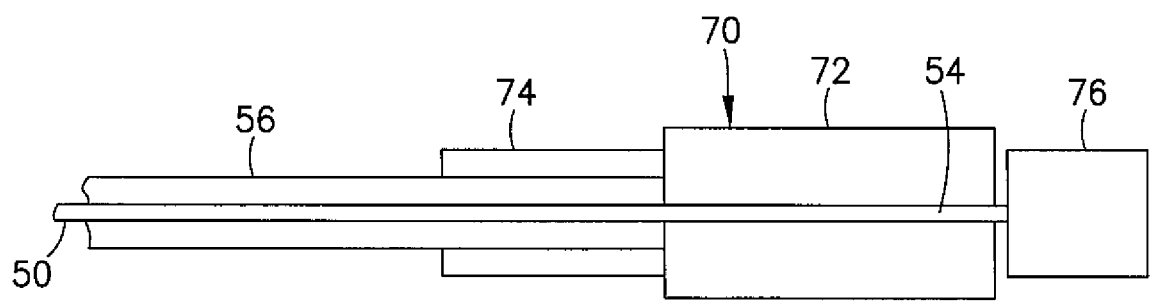
FIG. 5 is a schematic view illustrating connections of the sheath and basket device to the assembly shown in FIG. 4.

Referring also to FIGS. 4-5, the tool 36 in this example comprises a control assembly 70. The control assembly 70 is connected to proximal ends of the basket device 50 and sheath 56. The control assembly 70 is configured to be attached to the control section 12 at the port 60 into the working channel 24. Although the features will be described with reference to the example embodiments of the control assembly shown in the drawings, it should be understood that features can be embodied in many alternate forms of embodiments. In addition, any suitable size, shape or type of elements or materials could be used.

In this example the control assembly 70 comprises an outer sleeve 72, a connector 74 and a plunger 76. The connector 74 is configured to connect the control assembly 70 to the control section 12 at the port 60. The outer sleeve 72 is slidably connected to the connector 74 as indicated by arrow A in FIG. 4. In this example the proximal end of the sheath 56 is attached to the outer sleeve 72 to longitudinally move the sheath 56 when the outer sleeve 72 is moved. The plunger 76 is movably mounted to the outer sleeve 72 to also slide as indicated by arrow A. FIG. 4 shows the plunger 76 is an outward home position relative to the outer sleeve 72. From this outward home position the plunger 76 can be depressed into the outer sleeve 72 as indicated by arrow B. The proximal end of the shaft section 54 of the basket device 50 is attached to the plunger 76 for the plunger to be able to longitudinally move the shaft section 54 of the basket device 50 when the plunger 76 is longitudinally moved. Thus, when the plunger 76 is depressed relative to the outer sleeve 72, the distal end of the basket device 50 is extended out of the front end aperture 66 of the sheath 54. When the plunger 76 is not depressed, the distal end 52 of the basket device 50 is retracted towards the front end aperture 66 of the sheath 54.

In an alternate example, the proximal end of the sheath 56 may be connected to the plunger 76, and a proximal end of the shaft section 54 of the basket device 50 may be connected to the outer sleeve 72. In this alternate example the plunger 76 may be depressed from its extended home position towards its depressed position on the outer sleeve 72 to move the sheath 56 over the basket section 52, and the plunger may be released from its depressed position to its extended home position to move the sheath 56 off of the basket section 52.

Figure 6:
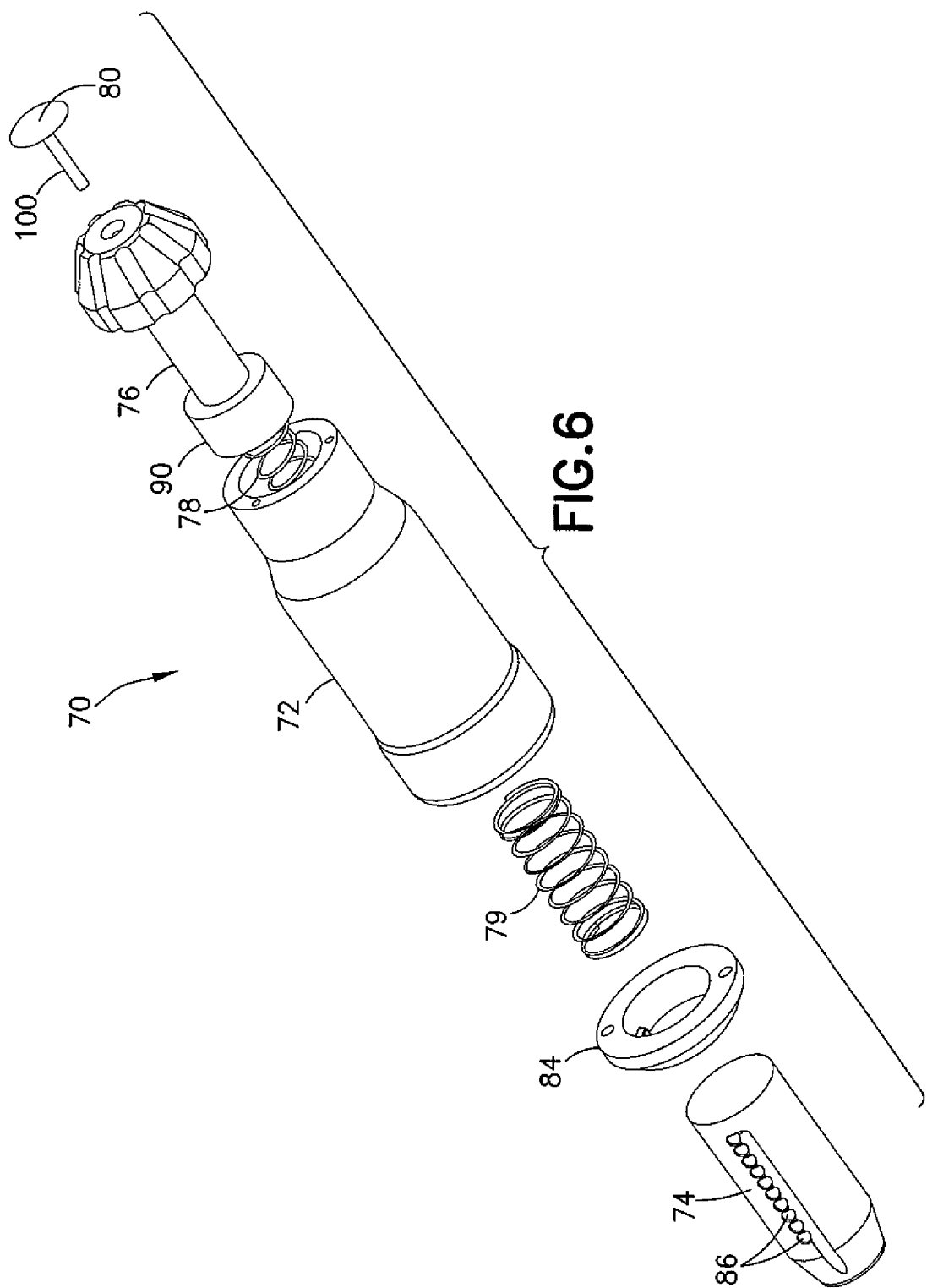
FIG. 6 is an exploded perspective view of the assembly shown in FIG. 4.
Figure 8:
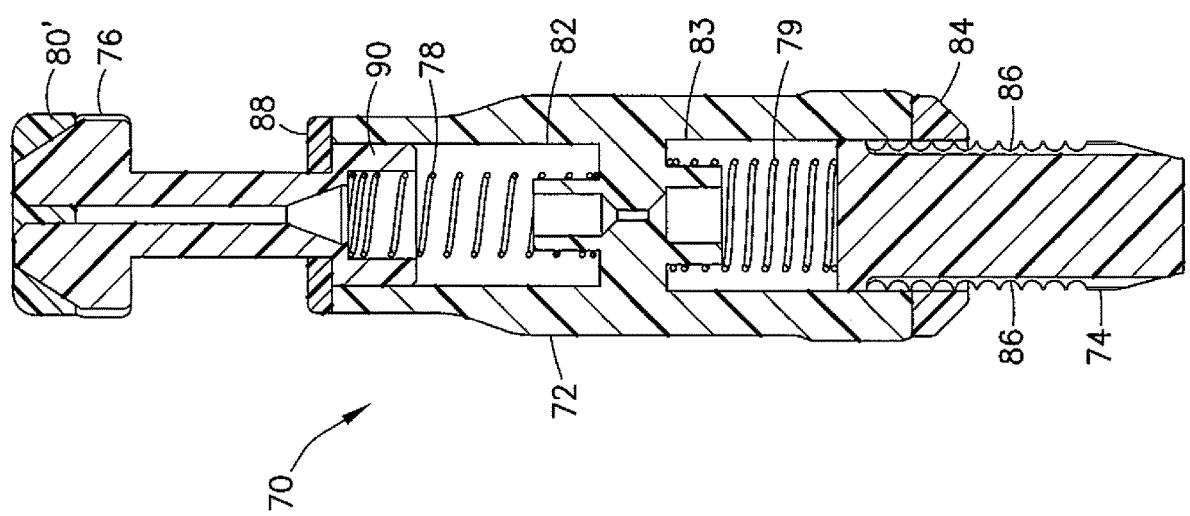
FIG. 8 is a cross sectional view of the assembly shown in FIGS. 4 and 6.
Figure 7:
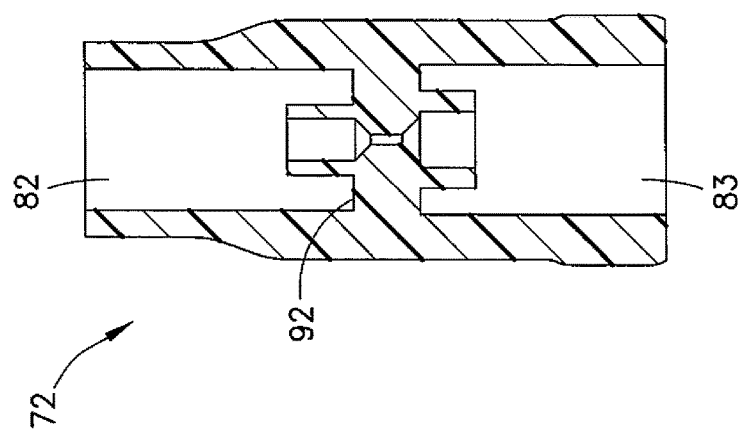
FIG. 7 is a cross sectional view of the outer sleeve of the assembly shown in FIGS. 4 and 6.

Referring also to FIG. 6 an exploded view of the control assembly 70 is shown. In the example shown, the control assembly 70 comprises two springs 78, 79 and a top button 80. Referring also to FIG. 7, the top spring 78 is located in area 82 of the outer sleeve 72 and the bottom spring 79 is located in the area 83 of the outer sleeve 72. This is also shown in FIG. 8, but with a slightly different button 80'. The top spring 78 is compressed between surface 92 shown in FIG. 7 and the bottom end 90 of the plunger 76 to bias the plunger 76 in its extending home position relative to the outer sleeve as shown in FIGS. 4 and 8. A top member 88 is connected to the top end of the outer sleeve 72 to keep the bottom end 90 of the plunger 76 inside the area 82.

The bottom spring 79 biases the outer sleeve 72 away from the connector 74. However, a bottom member 84 is connected to the bottom end of the outer sleeve 72. The bottom member 84 is adjustably located on the connector 74. The bottom member 84 has projections which are configured to engage recesses 86 in the connector 74 to adjustable lock the longitudinal position of the outer sleeve 72 on the connector 74 at one of a plurality of different longitudinal positions of the connector 74. In the example shown, the outer sleeve 72 can be axially rotated with the bottom member 84 to disengage from the recesses 86. Then, the outer sleeve 72 can be longitudinally slid along the connector 74 to a new longitudinal position. The outer sleeve 72 can then be axially rotated with the bottom member 84 in an opposite direct to reengage with a new pair of the recesses 86. This may be used to act as a fine adjustment for moving both the basket device 50 and sheath 56 together relative to the apparatus 10.

The top button 80 is attached to the top of the plunger 76. The top button 80 is adapted to axially rotate on the top of the plunger 76. FIGS. 4 and 6 show a top button 80 which covers less than half of the top side of the plunger. FIGS. 8 and 9 show a top button 80' which covers a majority of the top surface. However, both top buttons 80, 80' function the same way. In particular, the top buttons 80, 80' provide a top surface for a user's finger to press against, but still allow the plunger 76 to be easily axially rotated on the outer sleeve 72.

Figure 11:
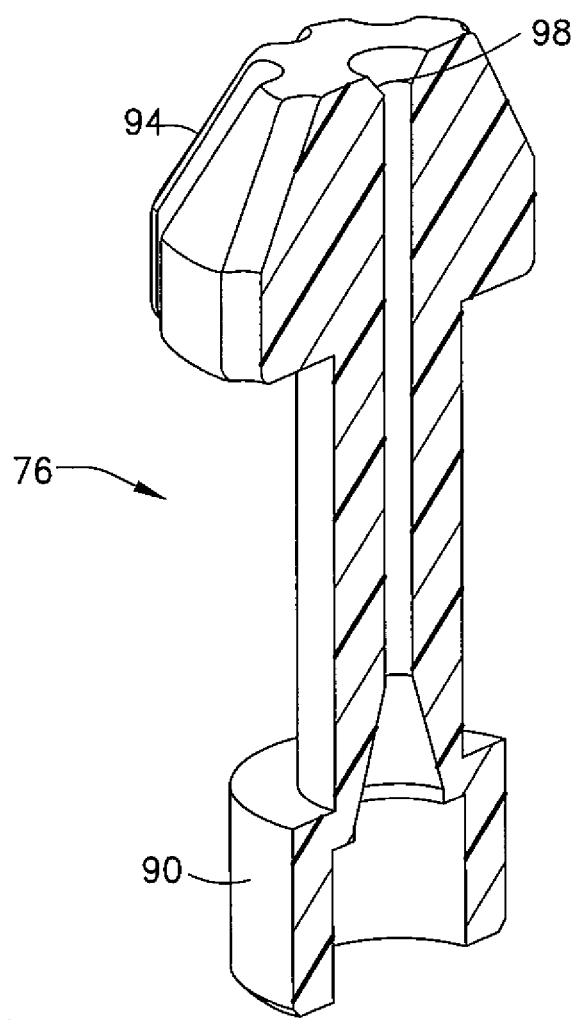
FIG. 11 is a cross sectional view of the plunger shown in FIG. 10.

As seen in FIGS. 9-11, the plunger 76 has a top end 94. The top end 94 has finger grooves 96 to provide better frictional engagement with a user's finger(s). The top end 94 has a hole 98. The top button 80, 80' has a projection 100 which extends into the hole 98. The button 80, 80' is rotatably mounted to the plunger 76 at this projection/hole interface. The proximal end of the shaft section 54 of the basket device 50 is fixedly connected to the plunger 76 in the channel leading to the hole 98. However, the shaft section 54 of the basket device 50 is not directly connected to the button 80, 80'. Thus, when the user has his or her finger on the button 80, 80', the user may axially rotate the basket device 50 by axially rotating the plunger 76 while the button 80, 80' and the user's finger on the button do not axially rotate. This provides a more comfortable feel to the user's finger and less possibility that the user's finger might slip off of the button/plunger assembly while the plunger is being rotated.

The above identified example embodiment provides a tool comprising a first controller and a second controller. The first controller is formed by a plunger and cylinder mechanism comprising the button 80 and the outer sleeve 72. This first controller is adapted to linearly move the basket device. The second controller is formed by the plunger 76 and is adapted to rotate the basket device independently of the first controller's control of the linear movement or position of the basket device 50. In the example described above, the plunger 76 connects the button 80 to the basket device 50 and the cylinder formed by the outer sleeve 72.

Figure 12:
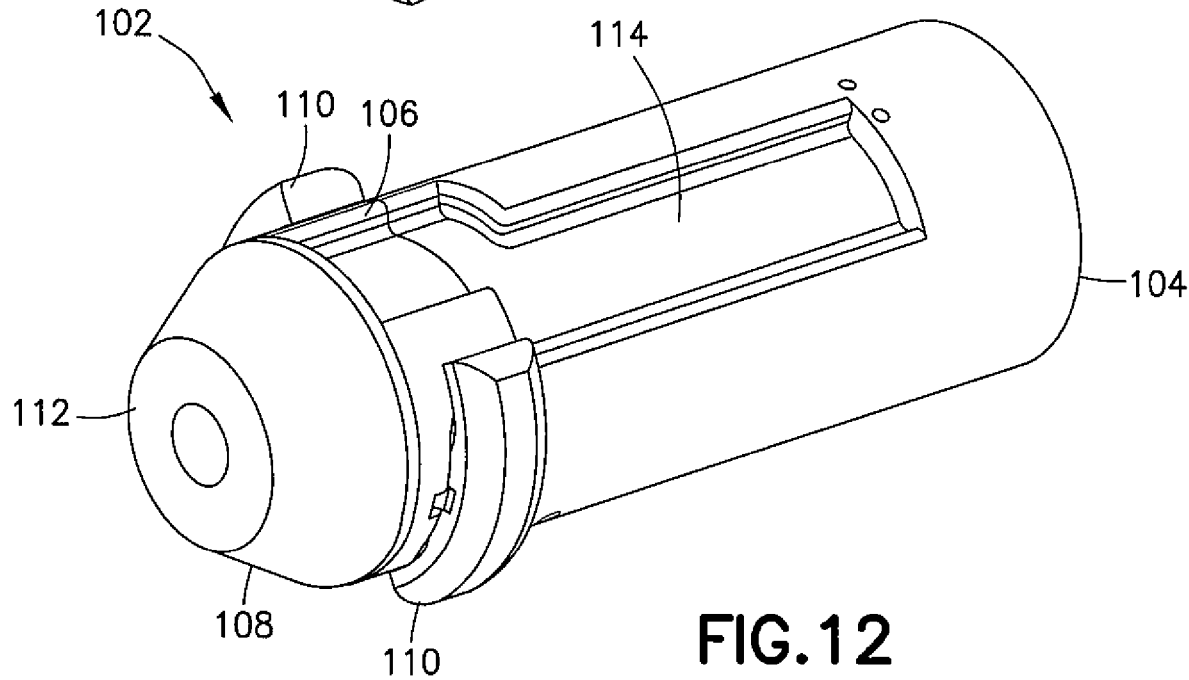
FIG. 12 is a perspective view of an alternate embodiment of the connector shown in FIGS. 4 and 8.
Figure 13:
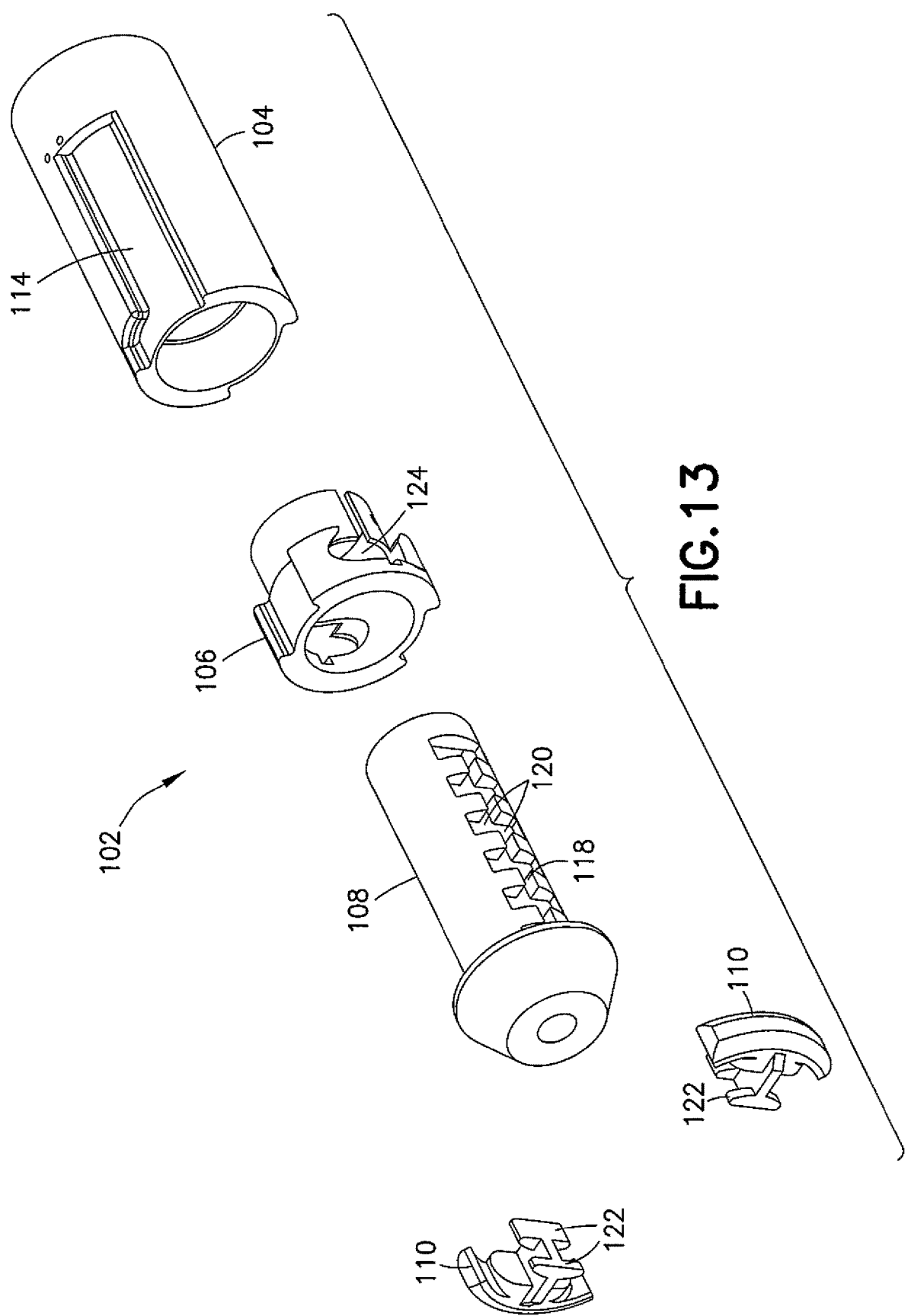
FIG. 13 is an exploded perspective view of the connector shown in FIG. 12.

Referring also to FIGS. 12 and 13, an alternate example of the connector is shown. In this example embodiment the connector 102 is configured to replace the connector 74. The connector 102 generally comprises an extension shaft 104, and inner insert 106, a plunger shaft 108 and two buttons 110. The front end 112 of the plunger shaft 108 is adapted to be located at the port 60 into the working channel 24. The inwardly facing projections of the bottom member 84 on the outer sleeve 72 are located in the grooves 114. The bottom spring 79 biases the outer sleeve 72 away from the extension shaft 104, but the inward projections on the bottom member 84 being located in the grooves 114 keeps the outer sleeve connected to the extension shaft 104. The bottom spring 79 may be compressed to move the outer sleeve 72 downward on the outside of the extension shaft 104. This allows the sheath 56 and basket device 50 to be moved together relative to the connector 102 and apparatus 10. The outer sleeve 72 and attached bottom member 84 may be axially rotated on the extension shaft 104 to move the inward projections on the bottom member 84 to rotate into areas 116 to lock the longitudinal position outer sleeve 72 on the connector 102 at a forward location.

The plunger shaft 108 comprises lateral slots 118 and teeth pockets 120 on opposite sides of the slots 118. The slots 118 allow for relative movement of the buttons 110 along the longitudinal length of the plunger shaft 108. The teeth pockets 120 allow the teeth 122 to engage in the teeth pockets 120 to adjustably lock the position of the buttons 110 relative to the plunger shaft 108. The buttons 110 project into the slots 118 through the button holes 124 in the inner insert 106. The buttons 110 may be outwardly biased by springs (not shown). The buttons 110 may be inwardly depressed to move the teeth 112 out of the teeth pockets 120 and allow longitudinal extension or retraction of the extension shaft 104 (with attached inner insert 106) along to the plunger shaft 108. This feature may be used to allow use of the tool with different endoscopes having different length working channels. The length of the connector 102 can be adjusted to adjust for the different length working channels. Thus, the tool can be used with different types of endoscopes.

With features as described herein, an endoscope tool may be provided having a spin plate, such as the plunger 76 for example, for axially rotating another member, such as a basket device for example. Features as described herein are not necessarily limited to a Surgeon Controlled Basket Device (SCBD). Features as described herein may be used to integrate into a single simplified design a plunger mechanism with an axial rotation mechanism.

In a conventional Surgeon Controlled Basket Device (SCBD) device, if the operator of the plunger style basket wants to hold the basket open and rotate the basket it is difficult to maintain a steady position and pressure of the finger on the plunger while the plunger is rotating.

With features as described herein, a mechanism may be provided which allows the operator's finger to keep pressure on the plunger while the plunger is rotated without subjecting the finger, used to maintain pressure, to the rotation. The top surface will spin independently relative to the plunger. This allows the plunger to be rotated freely without requiring adjustment by the finger used to apply the downward pressure. A top surface, such as button 80 or 80' for example, may be attached to the plunger in a manner which holds the top surface steady relative to the plunger in the direction of movement resulting in deployment of the basket (axial direction), but does not link the radial position of the top surface to the radial position or motion of the plunger mechanism. This allows the two components to rotate independent of each other while still maintaining a linear position relationship.

In one type of example embodiment a tool for use by a surgeon for operating a basket device for capturing an object to be removed from a body of an animal may be provided, the tool comprising a first controller adapted to be coupled to the basket device for selectively controlling the basket device and moving the basket device between a first, closed position and a second, open position, the first controller comprising: a plunger and cylinder mechanism; and a handle coupled to the plunger for operating the relative position of the plunger with respect to the cylinder; and a second controller positioned adjacent to the first controller and adapted to be coupled to the basket device for selectively controlling the rotation of the basket device independent of the first controller.

The tool may further comprise a sheath having a first end and a second end, the sheath adapted to receive the basket device and to have the basket device longitudinally slide with respect thereto between the first, closed position and the second, open position; and wherein the sheath is coupled to the first controller for translational movement relative to the basket device and the basket device is coupled to the second controller for rotational movement with respect to the first controller. The tool may further comprise a first biasing mechanism operatively located for biasing the plunger with respect to the cylinder to move the basket device toward the first, closed position. The tool may further comprise a locking mechanism coupled to the first controller for locking the plunger in the second, open position. The second controller may remain operative when the locking mechanism locks the first controller. The second controller may continue to rotate the basket device while the first controller is locked. The tool may further comprise a second biasing mechanism for biasing the basket device toward the first, closed position with respect to the handle and the sheath; and wherein the basket device is rigidly rotationally coupled to second controller. The second biasing mechanism may be coupled to the second controller to bias the plunger 76 towards moving the basket to a first, closed position. The tool may further comprise a luer coupler, such as connector 74 for example, for selectively coupling the tool to an endoscope.

An example embodiment may be provided in a tool for use by a surgeon for operating a basket device for capturing an object to be removed from a body of an animal, the tool comprising a housing having a longitudinal axis and including a passage; a first controller including a first portion located in the passage in the housing and a second portion extending from the housing; wherein the first controller is adapted to be coupled to the basket device for selectively controlling the basket device and wherein the first controller is axially movable in the passage of the housing for moving the basket device between a first, closed position and a second, open position, and wherein the first controller is rotationally movable in the passage of the housing for rotating the basket device when in the second, open position; and an end surface coupled to the second portion of the first controller wherein the end surface moves axially with the first controller and wherein the end surface moves independently rotationally of the first controller such that the end surface may remain rotationally stationary while the first controller is rotated.

The tool may further comprise a sheath having a first end and a second end, the sheath adapted to receive the basket device- and to have the basket device longitudinally slide with respect thereto between the first, closed position and the second, open position; and wherein the basket device is coupled to first controller for translational movement relative to the sheath and wherein the sheath is coupled to housing. The tool may further comprise a first biasing mechanism operatively located for biasing the first controller with respect to the passage in the housing to urge the basket device toward the first, closed position. The tool may further comprise a locking mechanism coupled to the housing for locking the first controller in the second, open position. The first controller may remain rotationally operative when the locking mechanism locks the first controller in the second, open position. The tool may further comprise a luer coupler for selectively coupling the tool to an endoscope.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. A tool for use by a surgeon for operating a basket device for capturing an object to be removed from a body of a human or an animal, the tool comprising:
   a first controller adapted to be coupled to the basket device for selectively controlling the basket device and moving the basket device between a first, closed position and a second, open position, the first controller comprising:
      a plunger and cylinder mechanism; and
      a handle coupled to a plunger of the plunger and cylinder mechanism, the handle operable to adjust a relative position of the plunger with respect to a cylinder of the plunger and cylinder mechanism;
      where linear actuation of the handle and the plunger relative to the cylinder controls linear movement of the basket device between the first and second positions;
   a biasing mechanism operatively located for biasing the plunger with respect to the cylinder to move the basket device toward the first, closed position;
   a second controller positioned adjacent to the first controller and adapted to be coupled to the basket device, where the second controller is axially rotatable on the handle, where axial rotation of the second controller relative to the handle adjusts a rotational position of the basket device independent of the first controller, and where the second controller is linearly movable with the plunger when the relative position of the plunger is moved with respect to the cylinder; and
   a locking mechanism coupled to the first controller for locking the plunger such that the basket device is in the second, open position wherein the second controller remains operative when the locking mechanism locks the first controller.

2. The tool of claim 1 further comprising:
   a sheath having a first end and a second end, the sheath adapted to receive the basket device and to have the basket device longitudinally slide with respect thereto between the first, closed position and the second, open position; and
   wherein the sheath is coupled to the first controller for translational movement relative to the basket device, and the basket device is coupled to the second controller for rotational movement with respect to the first controller.

3. The tool of claim 1
   wherein the basket device is rigidly rotationally coupled to the second controller.

4. The tool of claim 1 further comprising a luer coupler for selectively coupling the tool to an endoscope.

5. A tool for use by a surgeon for operating a basket device for capturing an object to be removed from a body of a human or an animal, the tool comprising:
   a housing having a longitudinal axis and including a passage;
   a first controller comprising an elongate controller body extending from a proximal end to a distal end, the distal end of the controller body located in the passage in the housing and the proximal end of the controller body extending outwardly from the housing, wherein the first controller is adapted to be coupled to the basket device for selectively controlling the basket device and wherein the first controller is axially movable in the passage of the housing for moving the basket device between a first, closed position and a second, open position, and wherein the first controller is rotationally movable in the passage of the housing for rotating the basket device when in the second, open position;
   an end surface coupled to the proximal end of the controller body, wherein the end surface is axially movable together with the first controller, and wherein the end surface is rotationally movable independently from the first controller such that the end surface remains rotationally stationary while the first controller is rotated; and
   a locking mechanism coupled to the housing for locking the first controller in the second, open position, wherein the first controller remains rotationally operative when the locking mechanism locks the first controller in the second, open position.

6. The tool of claim 5 further comprising:
   a sheath having a first end and a second end, the sheath adapted to receive the basket device and to have the basket device longitudinally slide with respect thereto between the first, closed position and the second, open position; and
   wherein the basket device is coupled to the first controller for translational movement relative to the sheath, and wherein the sheath is coupled to the housing.

7. The tool of claim 5 further comprising a biasing mechanism operatively located for biasing the first controller with respect to the passage in the housing to urge the basket device toward the first, closed position.

8. The tool of claim 5 further comprising a luer coupler for selectively coupling the tool to an endoscope.

9. A tool for use by a surgeon for operating a sheath and basket device assembly for capturing an object to be removed from a body of a human or an animal, the tool comprising:
   an outer sleeve, where the outer sleeve comprises a first cylinder at a first end and a second cylinder at an opposite second end, where the outer sleeve is configured to have a sheath of the sheath and basket device assembly connected thereto;

a connector slidably connected to the outer sleeve in the first cylinder at the first end of the outer sleeve, where the connector is configured to connect the tool to a port of an endoscope;

a plunger slidably connected to the outer sleeve in the second cylinder at the opposite second end of the outer sleeve, where the plunger is configured to have a proximal end of a basket device of the sheath and basket device assembly connected thereto;

a first spring biasing the outer sleeve in a direction away from the connector; and a second spring biasing the plunger in an outward direction relative to the outer sleeve;

where the plunger is configured to longitudinally slide in the second cylinder and axially rotate relative to the outer sleeve, where the outer sleeve is configured to longitudinally move on the connector with the connector longitudinally sliding in the first cylinder, where movement of the outer sleeve relative to the connector is configured to move the sheath and the basket device relative to the connector, and where movement of the plunger relative to the outer sleeve is configured to move the basket device relative to the sheath.

10. The tool as in claim 9 where the plunger is configured to both axially rotate the basket device relative to the sheath and longitudinally slide the basket device relative to the sheath.

11. The tool as in claim 9 where the outer sleeve forms a handle for moving the outer sleeve towards the connector.

12. The tool as in claim 11 where the plunger forms a button configured to be depressed into the outer sleeve, and where the button is configured to be rotated by a user relative to the outer sleeve.

\* \* \* \* \*